United States Patent
Kasic, II et al.

(10) Patent No.: US 6,537,201 B1
(45) Date of Patent: Mar. 25, 2003

(54) IMPLANTABLE HEARING AID WITH IMPROVED SEALING

(75) Inventors: James Frank Kasic, II, Boulder, CO (US); José H. Bedoya, Boulder, CO (US); Douglas Alan Miller, Lafayette, CO (US); James Roy Easter, Lyons, CO (US)

(73) Assignee: Otologics LLC, Boulder, CO (US)

( * ) Notice: Subject to any disclaimer, the term of this patent is extended or adjusted under 35 U.S.C. 154(b) by 0 days.

(21) Appl. No.: 09/991,397

(22) Filed: Nov. 20, 2001

Related U.S. Application Data
(60) Provisional application No. 60/325,844, filed on Sep. 28, 2001.

(51) Int. Cl.⁷ .............................................. H04R 25/00
(52) U.S. Cl. ............................................. 600/25
(58) Field of Search ................ 338/162, 174, 338/199; 600/25; 623/10; 607/56, 137, 55, 57, 115, 136; 381/68–68.3, 312, 322, 324, 328

(56) References Cited

U.S. PATENT DOCUMENTS

| | | | |
|---|---|---|---|
| 4,180,700 A | 12/1979 | Kraska et al. ............ 174/152 |
| 4,217,137 A | 8/1980 | Kraska et al. ............ 75/165 |
| 4,532,930 A | 8/1985 | Crosby et al. ............ 128/419 |
| 4,678,868 A | 7/1987 | Kraska et al. ............ 174/152 |
| 4,785,827 A | 11/1988 | Fischer ............ 128/783 |
| 4,991,582 A | 2/1991 | Byers et al. ............ 128/419 |
| 5,046,242 A | 9/1991 | Kuzma ............ 29/878 |
| 5,069,210 A | 12/1991 | Jeutter et al. ............ 128/420.6 |
| 5,105,811 A | 4/1992 | Kuzma ............ 128/420.6 |
| 5,277,694 A | 1/1994 | Leysieffer et al. ............ 600/25 |
| 5,282,858 A | 2/1994 | Bisch et al. ............ 623/10 |
| 5,324,316 A | 6/1994 | Schulman et al. ............ 607/61 |
| 5,338,287 A | 8/1994 | Miller et al. ............ 600/25 |
| 5,456,654 A | 10/1995 | Ball ............ 600/25 |
| 5,513,793 A | 5/1996 | Malmgren ............ 228/193 |
| 5,531,787 A | 7/1996 | Lesinski et al. ............ 623/10 |
| 5,549,658 A | 8/1996 | Shannon et al. ............ 607/57 |
| 5,558,618 A | 9/1996 | Maniglia ............ 600/25 |
| 5,562,716 A | 10/1996 | Kuzma ............ 607/36 |
| 5,624,376 A | 4/1997 | Ball et al. ............ 600/25 |
| 5,738,270 A | 4/1998 | Malmgren ............ 228/193 |
| 5,772,575 A | 6/1998 | Lesinski et al. ............ 600/25 |
| 5,781,099 A | * 7/1998 | Joschika et al. ............ 338/162 |
| 5,795,287 A | 8/1998 | Ball et al. ............ 600/25 |
| 5,800,336 A | 9/1998 | Ball et al. ............ 600/25 |
| 5,814,095 A | 9/1998 | Müller et al. ............ 607/57 |
| 5,833,714 A | 11/1998 | Loeb ............ 607/56 |
| 5,857,958 A | 1/1999 | Ball et al. ............ 600/25 |
| 5,859,916 A | 1/1999 | Ball et al. ............ 381/326 |
| 5,881,158 A | 3/1999 | Lesinski et al. ............ 381/174 |
| 5,897,486 A | 4/1999 | Ball et al. ............ 600/25 |
| 5,906,635 A | 5/1999 | Maniglia ............ 607/57 |
| 5,913,815 A | 6/1999 | Ball et al. ............ 600/25 |
| 5,951,601 A | 9/1999 | Lesinski et al. ............ 623/10 |
| 5,957,958 A | 9/1999 | Schulman et al. ............ 607/56 |
| 6,005,955 A | 12/1999 | Kroll et al. ............ 381/328 |

* cited by examiner

Primary Examiner—Eric F. Winakur
Assistant Examiner—Nikita R Veniaminov
(74) Attorney, Agent, or Firm—Marsh Fischmann & Breyfogle LLP

(57) ABSTRACT

An improved implantable hearing aid apparatus and related method of manufacture are disclosed. The inventive apparatus and method utilize electrodeposition techniques to yield enhanced sealing of implanted componentry. In one embodiment an inventive apparatus comprises at least first and second implantable hearing aid component housing members having at least one electrodeposited layer overlapping adjacent portions of the housing members to provide a hermetic seal therebetween. In another embodiment an inventive apparatus comprises an implantable hearing aid component housing member formed via electrodeposition having a plurality of electrodeposited layers, wherein at least two adjacent ones of the layers comprise differing materials (e.g. to yield enhanced functional characteristics). By way of primary example, a hollow bellows of any implantable middle ear actuator may be formed via the sequential electrodeposition of multiple layers on a shaped mandrel which is then selectively removed (e.g., via a removal fluid).

30 Claims, 8 Drawing Sheets

IMPLANTABLE HEARING AID WITH IMPROVED SEALING

RELATED APPLICATION

This application claims priority from U.S. Provisional Patent Application Ser. No. 60/325,844, filed on Sep. 28, 2001, which is incorporated herein by reference.

FIELD OF THE INVENTION

The present invention relates to the field of implantable hearing aid devices, and more specifically to the sealing of implantable hearing aid componentry housings and interconnections therebetween. The invention is particularly apt for use in conjunction with implantable hearing aid actuator bellows.

BACKGROUND OF THE INVENTION

Implantable hearing aid systems entail the subcutaneous positioning of various componentry on or within a patient's skull, typically at locations proximal to the mastoid process. Such componentry typically includes a receiver for receiving transcutaneous RF and/or acoustic signals and an interconnected processor to provide processed signals. Additionally, some form of actuator is employed to utilize the processed signals to stimulate the ossicular chain and/or tympanic membrane within the middle ear of a patient.

By way of example, one type of implantable actuator comprises an electromechanical transducer having a vibratory member positioned to mechanically stimulate the ossicular chain via axial vibrations. (see e.g., U.S. Pat. No. 5,702,342). In another approach, implanted excitation coils may be employed to electromagnetically stimulate magnets affixed within the middle ear. Additional implantable componentry may include one or more power storage components and associated recharging componentry. Components of the above-noted nature may be utilized in either semi-implantable systems which utilize additional external mounted componentry (e.g. microphones and transmitters located in behind-the-ear units) and fully-implantable systems which do not employ external componentry during normal usage.

As may be appreciated, reliable operation of implanted hearing aid componentry is extremely important to the long term viability and widespread utilization of implanted hearing aid systems. Such reliability is key from the perspective of not only achieving ongoing enhanced hearing, but additionally due to the high costs associated with surgical procedures attendant to the servicing/repair of implanted components.

In conjunction with achieving high reliability, the need to isolate implanted componentry from bodily fluids has been recognized (see e.g. U.S. Pat. No. 5,282,858). While significant advances have been made to enclose implanted componentry in sealed housings, the present inventors have devised further improved techniques to realize enhanced sealing in implantable hearing aid systems. Such techniques include the capability to achieve reliable sealing while allowing for relative movement between mechanically interconnected hearing aid componentry. In the later regard, the inventive techniques are particularly well-suited for implementation in implanted hearing aid systems that include a bellows to facilitate axial vibration of a vibratory member of an electromechanical transducer actuator.

SUMMARY OF THE INVENTION

In view of the foregoing, a general objective of the present invention is to provide an implantable hearing aid apparatus with improved sealing, thereby yielding enhanced reliability.

A further objective of the present invention is to provide an improved implantable hearing aid while maintaining or even reducing overall mass and complexity.

Another objective of the present invention is to provide an improved implantable hearing aid that can be produced in a highly consistent manner.

Yet a further objective of the present invention is to provide an improved implantable hearing aid apparatus that accommodates relative movement between implanted housing members while enhancing the sealing therebetween.

In relation to realizing the above-identified objectives, the present inventors have recognized that significant advances are achievable through the utilization of electrodeposition techniques. Specifically, it has been recognized that electrodeposition may be advantageously utilized to both sealably interconnect implanted hearing aid componentry housing members and in the fabrication of multi-layered implanted hearing aid housing members.

Based on such recognition, and in one aspect of the present invention, an implantable hearing aid apparatus is provided that comprises first and second implantable hearing aid component housing members, and at least one electrodeposited layer overlapping adjacent portions of the first and second housing members to provide an interconnection and hermetic seal therebetween. Preferably, the outer electrodeposited layer may comprise a biocompatible first material, such as a biocompatible metal selected from a first metals group consisting of gold, platinum and titanium.

In conjunction with this inventive aspect, an outer electrodeposited layer and a conformal underlying electrodeposited layer may be provided, wherein the outer layer comprises a first material that is different than a second material comprising the underlying layer. Preferably, the outer layer hermetically seals the underlying layer. Further, the underlying layer may be provided to have at least one of a modulus of elasticity, tensile strength and yield strength that is at least two times greater than that of the electrodeposited outer layer. By way of primary example, the underlying electrodeposited layer may comprise a second material selected from a second metals group consisting of nickel, iron, chromium, platinum, iridium, copper and aluminum. Such an arrangement may be of benefit where a degree of relative movement between the housing members is desired.

In addition to an outer layer and underlying layer, a conformal inner electrodeposited layer may also be provided to hermetically seal the underlying layer between the outer layer and inner layer. As with the outer layer, the inner layer may comprise a biocompatible metal selected from the noted first metals group.

Of note, the first and second housing members may be advantageously configured to define a substantially flush interface region therebetween. Further, the electrodeposited layers(s) overlapping the interface region may be provided to be substantially, continuously arcuate and/or flat. By way of example, opposing ends of tubular first and second cylindrical housing members may be disposed in abutting relation, wherein one or more electrodeposited layer(s) is disposed across and about the abutting ends of the first and second housing members.

In one embodiment, one of the first and second housing members may be in the form of a hollow bellows employed in an electromechanical transducer actuator with a vibratory member extending therethrough. The hollow bellows may comprise a plurality of undulations which allow the bellows to respond in an accordion-like fashion to axial vibrations imparted to one end thereof (e.g. via mechanical interconnection with the vibratory member). In such embodiment, the other one of the first and second housing members may be in the form of a sleeve member that is interconnected to one of an electromechanical transducer housing or to a distal end of the vibratory member that extends from the electromechanical transducer housing and through the hollow bellows and other housing member. Such sleeve member may advantageously comprise a biocompatible metal selected from the noted first metals group.

In another aspect of the present invention, an improved implantable hearing aid apparatus is provided that comprises first and second implantable hearing aid component housing members and a third implantable hearing aid component housing member interconnected therebetween. Specifically, the third housing member may be connected at a proximal end to the first housing member and at a distal end to the second housing member. Of importance, the third housing member may advantageously comprise a plurality of electrodeposited layers, wherein at least two adjacent ones of the plurality of electrodeposited layers comprise differing materials.

Preferably, an outer electrodeposited layer of the third housing member comprises a biocompatible material which substantially covers and thereby hermetically seals an underlying layer. Again, the underlying layer may be advantageously provided to have at least one of a modulus of elasticity, yield strength and tensile strength that is at least two times greater than that of the outer layer. By way of primary example, the outer layer may comprise a biocompatible metal selected from the first metals group identified above, and the underlying layer may comprise a metal selected from the second metals group noted above. The described, arrangement allows for relative axial movement of between the proximally/distally disposed first housing member/second housing member, respectively, while also yielding a reliably sealed structure.

In addition to the outer layer and underlying layer, an inner electrodeposited layer may also be provided to substantially cover and thereby hermetically seal the underlying layer. Preferably, the inner layer may comprise a biocompatible metal selected from the first metals group. As may be appreciated, the provision of a biocompatible inner layer that seals the underlying layer serves to preserve the functional integrity of the underlying layer in the event of bodily fluid leakage into the third housing member.

In conjunction with this inventive aspect, one or both of the first and second housing members, and the third housing member, may be configured to define a substantially flush interface region between adjacent portions thereof. Relatedly, at least one electrodeposited layer may be disposed in overlapping relation across the interface regions. By way of primary example, one end of each of the first and second housing members may be cylindrically configured to conformally abut opposing cylindrical ends of the third housing member, wherein biocompatible electrodeposited layers are disposed in a substantially continuous and arcuate manner over each of the two interface regions.

In one embodiment the third housing member may be in the form of a hollow bellows employed in an electromechanical transducer actuator with a vibratory member extending therethrough. The hollow bellows may comprise a plurality of undulations which allow the bellows to respond in an accordion-like fashion to axial vibrations imparted to one end thereof. More particularly, the proximal end of the bellows may be interconnected to (e.g. rigidly anchored) to an electromechanical transducer housing via a first housing member in the form of a tubular sleeve. The distal end of the bellows may be interconnected (e.g. rigidly) to the distal end of the vibratory member via a second housing member in the form of a tubular sleeve, wherein the vibratory member extends through all three housing members from the electromechanical transducer housing to communicate axial vibrations (e.g. to the ossicular chain within a patient's middle ear).

In view of the foregoing, it will be appreciated that an inventive method is also provided for use in the manufacture of implantable hearing aid apparatus. In one aspect, the inventive method includes the steps of positioning first and second implantable hearing aid component housing members in adjacent relation, and electrodepositing at least a first layer of a first material on adjacent portions of the first and second housing members to establish an interconnection and hermetic seal therebetween. The method may further provide for the electrodeposition of a second layer of a second material on the first layer, wherein the first and second materials are different. Additionally, a third electrodeposited layer may be disposed on the second layer.

Where a single layer is utilized to provide a hermetical seal and interconnection between the first and second implantable hearing aid component housing members, it is preferable for such layer to comprise a biocompatible metal selected from the noted first metals group. Where two electrodeposited layers of differing materials are utilized, the underlying layer may have at least one of a modulus of elasticity, tensile strength and yield strength that is at least two times greater than that of the outer layer. Again, the underlying layer may comprise a metal selected from the second metals group.

In another aspect of the inventive method a first implantable hearing aid component housing member may be formed by electrodepositing at least a first layer of a first material onto a supporting shaped mandrel, and by selectively removing the shaped mandrel from within the shaped first layer. As may be appreciated the shaped first layer may integrally define an internal space. For such purposes, the shaped mandrel may be of a hollow configuration. In turn, the removing step may be advantageously completed by contacting the shaped mandrel with a removal fluid (e.g. so that the mandrel material may be flowed away with the fluid), thereby facilitating the formation of complex housing configurations. In this regard, the removing step may comprise one of chemically removing, dissolving and melting the shaped mandrel away from the shaped first layer, e.g. by flowing the removal fluid through the hollow shaped mandrel.

More particularly, the removal fluid may be an appropriate reagent for leaching the shaped mandrel off of the shaped first layer. For such purposes, the electrodeposited first material comprising the first layer should be chemically inert to the removal fluid. In one example, the shaped mandrel may comprise aluminum, and the reagent may comprise sodium hydroxide.

Alternatively, the removal fluid may comprise a solvent for selectively dissolving the shaped mandrel apart from the shaped first layer. For example, the mandrel may comprise an electrically conductive plastic composite and the solvent may comprise tetraethylene.

In another option, the shaped mandrel may comprise a low-melting point metal, such as iridium. The shaped mandrel may be heated above its melting point and removed from the first shaped layer via a removal fluid that is flowed thereby.

In conjunction with this aspect of the inventive method, a second layer of a second material may also be electrodeposited on the first layer in the formation of the first housing member, wherein the first and second materials are different. Further, a third layer (e.g. comprising a first material) may be electrodeposited on to the second layer in the formation of the first housing member.

As may be appreciated, the first material may comprise a metal selected from the above-noted first metals group, while the second electrodeposited layer may comprise a material selected from the above-noted second metals group. Such an arrangement facilitates the above-noted sealing and relative movement functionalities. Preferably, the first, second, and third layers may be sequentially electrodeposited over the shaped mandrel prior to selective removal of the supporting shaped mandrel.

The inventive method may further provide for the positioning of a second implantable hearing aid component housing member in adjacent relation to one end of the first housing member, and the electrodeposition of at least one overlapping layer of a first material (e.g. selected from the above-noted first metals group) on abutting end portions of the first and second housing members to establish an interconnection and hermetic seal therebetween. Further, a third implantable hearing aid component housing member may be then positioned in adjacent relation to another end of the first housing member, wherein at least one overlapping layer of a first material (e.g. selected from the above-noted first metals group) is electrodeposited on abutting end portions of the first and third housing members to establish an interconnection and hermetic seal therebetween.

Preferably, a central portion of the first housing member, as well as the non-abutting end portions of the second and third housing members (i.e. not abutting the first housing member) may be covered prior to the electrodeposition of the noted overlapping layers. Further, the overlapping layers may be simultaneously formed prior to the selective removal of the shaped mandrel, wherein the second and third housing members each comprise a material(s) that is not subject to removal by a removal fluid.

In one embodiment, the inventive method may be employed in the manufacture of an implantable actuator arrangement having a bellows (e.g. comprising three electrodeposited layers) interconnected at a proximal end to an electromechanical transducer housing via a proximal tubular sleeve, wherein an electrodeposited layer overlaps the bellows and proximal sleeve. A distal end of the bellows is interconnected to a vibratory member (e.g. that extends from the transducer housing) via a distal tubular sleeve, wherein an electrodeposited layer overlaps the bellows and distal sleeve. Such an arrangement yields a highly reliable actuator.

In an additional aspect of the inventive method, one or more of the noted electrodeposited layers may be formed in a plurality of substeps, wherein the electrodeposition process is interrupted then restarted between each sub-step so as to affect a discontinuity in grain pattern formation and thereby reduce incidences of pore alignment. By way of example, such interruption and restarting may simply entail the application, discontinuance, and re-application of an electrical current to a metallic shaped mandrel in a submersion electrodeposition bath process. Additionally and/or alternatively, one or more of the above-noted electrodeposited layers may be established utilizing a pulsed current (e.g. as opposed to a direct current), wherein nucleation may occur between each pulse to reduce the likelihood of pore formation.

In yet a further related aspect of the inventive method, the above-noted, multi-layered first housing member may be subjected to hot isostatic pressing to improve the fatigue characteristics thereof. More particularly, the multi-layered first housing member may be subjected to an elevated temperature and pressure to enhance the microstructure of one or more of the electrodeposited layers. The temperature and pressure utilized should be selected so that the yield strength of the intended affected layer (e.g. the second of three layers) is less than the treatment pressure at the treatment temperature. HIP processing may also be utilized to treat the noted second and third housing members too.

Numerous additional aspects and advantages will become apparent to those skilled in the art upon consideration of the further description below.

DETAILED DESCRIPTION

Figure 1:
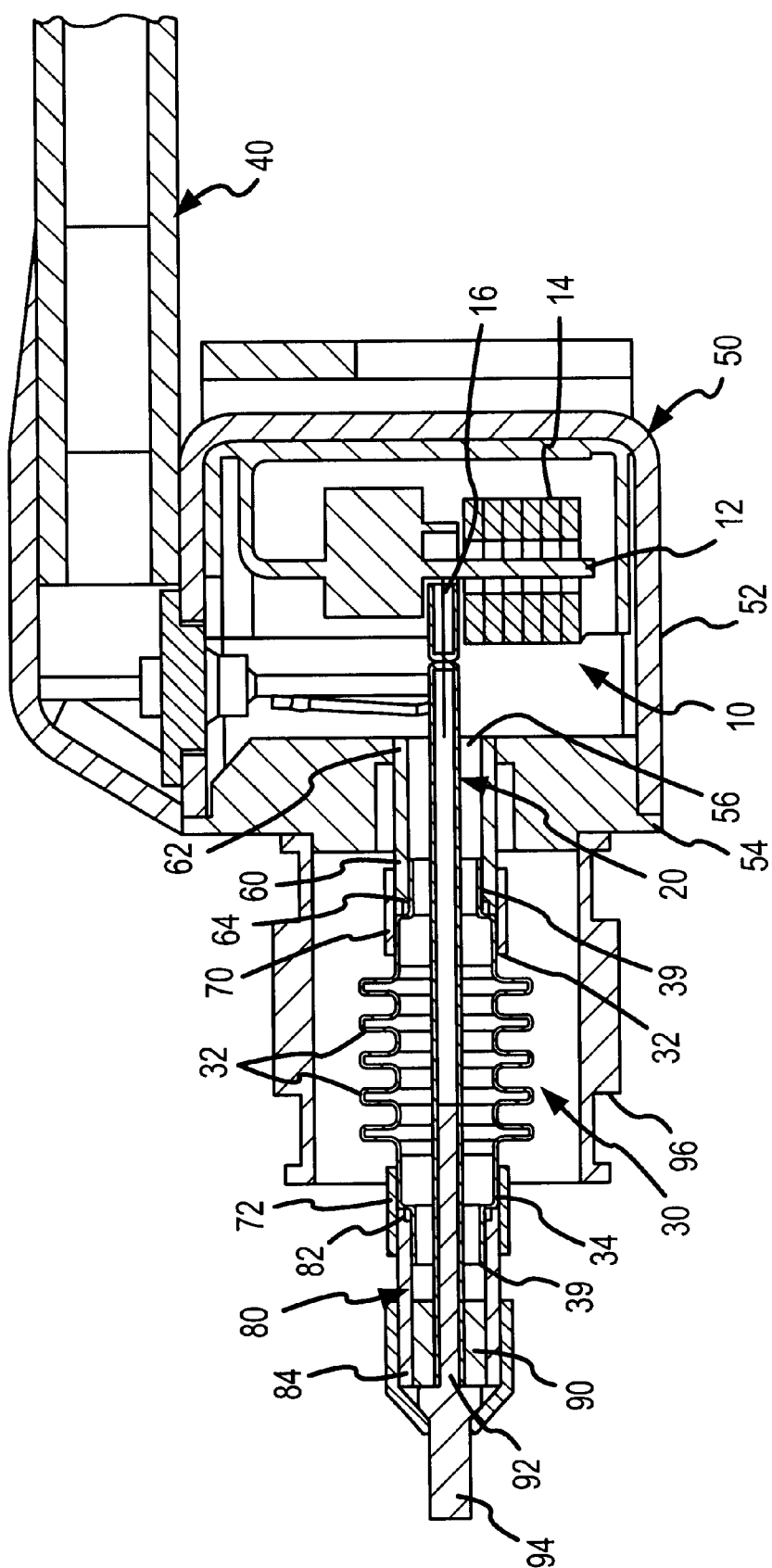
FIG. 1 is a cross-sectional side view of an implantable hearing aid actuator embodiment comprising features of the present invention.

FIG. 1 illustrates an implantable hearing aid actuator comprising one embodiment of the present invention. As may be appreciated, the embodiment may be employed in either semi-implantable or fully-implantable hearing aid systems.

The illustrated actuator includes an electrometrical transducer 10, an elongated vibratory member 20 interconnected at a proximal end to the transducer 10, and a hollow bellows 30 interconnected at its distal end to a distal end of the vibratory member 20. In use, the distal end of vibratory member 20 may be positioned within the middle ear of a patient to stimulate the ossicular chain. More particularly, transducer 10 may selectively induce axial vibrations of vibratory member 20, which vibrations are in turn communicated to the incus bone of the ossicular chain to yield enhanced hearing. Bellows 30 comprises a plurality of undulations 32 that allow bellows 30 to axially respond in an accordion-like fashion to axial vibrations of the vibratory member 20. Of note, bellows 30 is sealed to provide for isolation of the internal componentry of transducer 10.

In the latter regard, an electromechanical transducer 10 is shown that comprises a leaf 12 extending through a plurality of coils 14. Coils 14 may be electrically interconnected to a cable 40 which provides signals that induce a desired magnetic field across coils 14 so as to affect desired movement of leaf 12. In the illustrated embodiment, leaf 12 is connected to a stiff wire 16, and vibratory member 20 is crimped onto the wire 16. As such, movement of leaf 12 affects axial vibration of vibratory member 20.

Transducer 10 is disposed within a housing 50, comprising welded main body and lid housing members 52 and 54. In order to affect the communication of axial vibrations, vibratory member 20 passes through an opening 56 of the lid housing member 54 and extends through the bellows 30 to the distal end interconnection therewith. To maintain isolation of transducer 10 within housing 50, bellows 30 is hermetically sealed and hermetically interconnected to the housing 50 at its proximal end 32 and to the vibratory member 20 at its distal end 34.

More particularly, a proximal sleeve 60 may be welded at its proximal end 62 to transducer lid housing member 54 about the opening 56. Preferably, proximal sleeve 60 and housing members 52 and 54 all comprise the same biocompatible metal, such as titanium. An end portion, or tang 31, of the proximal end 32 of bellows 30 is slidably and intimately disposed within a cylindrical distal end 64 of proximal sleeve 60. As shown, the proximal end 32 of bellows 30 may be of a stepped-in, cylindrical configuration, wherein the distal end 64 of proximal sleeve 60 may abut the bellows 30 to define a substantially flush, annular interface region therebetween. Such an arrangement accommodates the application and reliability of an overlapping electrodeposited layer 70 (e.g., comprising a biocompatible material such as gold) disposed across and about the abutment region for interconnection and sealing purposes.

Similarly, a distal sleeve 80 may be slidably and intimately disposed about an end portion, or tang 33, of the distal end 34 of bellows 30. The distal end 34 may be of a stepped-in, cylindrical configuration, to define the tang 33, wherein a cylindrical proximal end 82 of distal sleeve 80 may abut the bellows 30 to define a substantially flush, annular interface region therebetween. Again, a reliable overlapping electrodeposited layer 72 (e.g., comprising a biocompatible material such as gold) may be readily provided across and about the abutment region for interconnection and sealing purposes.

In the illustrated embodiment, a cylindrical distal end 84 of distal sleeve 80 receives a cylindrical bushing 90, which locates the distal end of vibratory member 20 therewithin. As further shown, a wire member 92 may be provided within the distal end portion of vibratory member 20, wherein the distal extreme of distal sleeve 80, bushing 90, vibratory member 20 and wire member 92 collectively provide a substantially uninterrupted surface for a fusion weld interconnection (e.g. as may be achieved by laser welding) therebetween, thereby sealing the distal end of distal sleeve 80 and bellows 30.

The embodiment shown in FIG. 1 also includes a tip assembly 94 having an interconnected tip member 94a and cap member 94b, and a ring member 94c. The cap member 94b may be interconnected (e.g., via tack welding) about the distal end 84 of distal sleeve 80. The ring member 94c locates the tip assembly 94 relative to the distal extreme of sleeve 80. The tip member 94a may be particularly adapted for tissue attachment with the ossicular chain of a patient.

As noted above, bellows 30 functions to facilitate axial vibration of vibratory member 20 while maintaining isolation of transducer 10. To further address such functionality, reference will now be made to FIG. 2. As illustrated therein, bellows 30 may comprise a plurality of conformally disposed layers. Specifically, an inner layer 31, intermediate layer 33 and outer layer 35 may be advantageously provided via electrodeposition on a shaped mandrel 200, wherein adjacent ones of the inner layer 31, intermediate layer 33 and outer layer 35 comprise dissimilar materials. Outer layer 35 may comprise a biocompatible material that is substantially chemically inert to bodily fluids, thereby protecting intermediate layer 33. Similarly, inner layer 31 may be provided to display the same qualities. The provision of inner layer 31 serves to protect intermediate layer 33 in the event of undesired bodily fluid passage into bellows 30.

Intermediate layer 33 may comprise a material that provides enhanced flexural and strength characteristics relative to the inner and outer layers 31 and 35. More particularly, intermediate layer 33 may comprise a material that displays a relatively high modulus of elasticity, yet sufficient yield and tensile strength. As may be appreciated, such qualities are desirable in relation to bellows 30 ability to repeatedly and reliably respond in an accordion-like fashion to axial vibrations communicated thereto from the distal end of vibratory member 20.

In this regard, intermediate layer 33 may be advantageously provided to have a modulus of elasticity which is at least about two times the modulus of elasticity of the inner layer 31 and/or outer layer 35. Further, the intermediate layer 33 may be provided to display tensile and yield strengths which are otherwise at least about two times that of the inner layer 31 and/or outer layer 35.

By way of example, intermediate layer 33 may preferably comprise one or more metal selected from a group consisting of: nickel, iron, chromium, platinum, iridium, copper and aluminum. Inner layer 31 and outer layer 35 may preferably comprise one or more conductive materials selected from a group consisting of gold, titanium and platinum. While less desirable, other materials may also be utilized for layers 31, 33 and 35.

As will be further described, the inner layer 31, intermediate layer 33 and outer layer 35 of bellows 30 may be advantageously defined by a sequential electrodeposition process. In conjunction with such processing, a preferred thickness range for each of the layers may be established between about 5 to 50 microns, and even more preferably between about 5 to 20 microns. Further, a preferred thickness range for the electrodeposited layers 70 and 72 may be established at between about 5 to 50 microns, and even more preferably between about 20 to 40 microns.

In one arrangement, thicknesses of about 8 to 15 microns for each of the layers 31, 33 and 35 provides satisfactory results. In such arrangement, nickel may be employed for the intermediate layer 33 to provide a modulus of elasticity (in tension) of at least about 200 gigapascals with yield and tensile strengths of at least about 60 megapascals and 320 megapascals, respectively. Gold may be utilized for the inner and outer layers 31 and 35 to provide a modulus of elasticity (in tension) of at least about 80 gigapascals and a tensile strength of about 100 megapascals. Similarly, gold may be utilized to define the electrodeposited layers 70 and 72, with thicknesses of about 20 to 40 microns.

Figure 3:
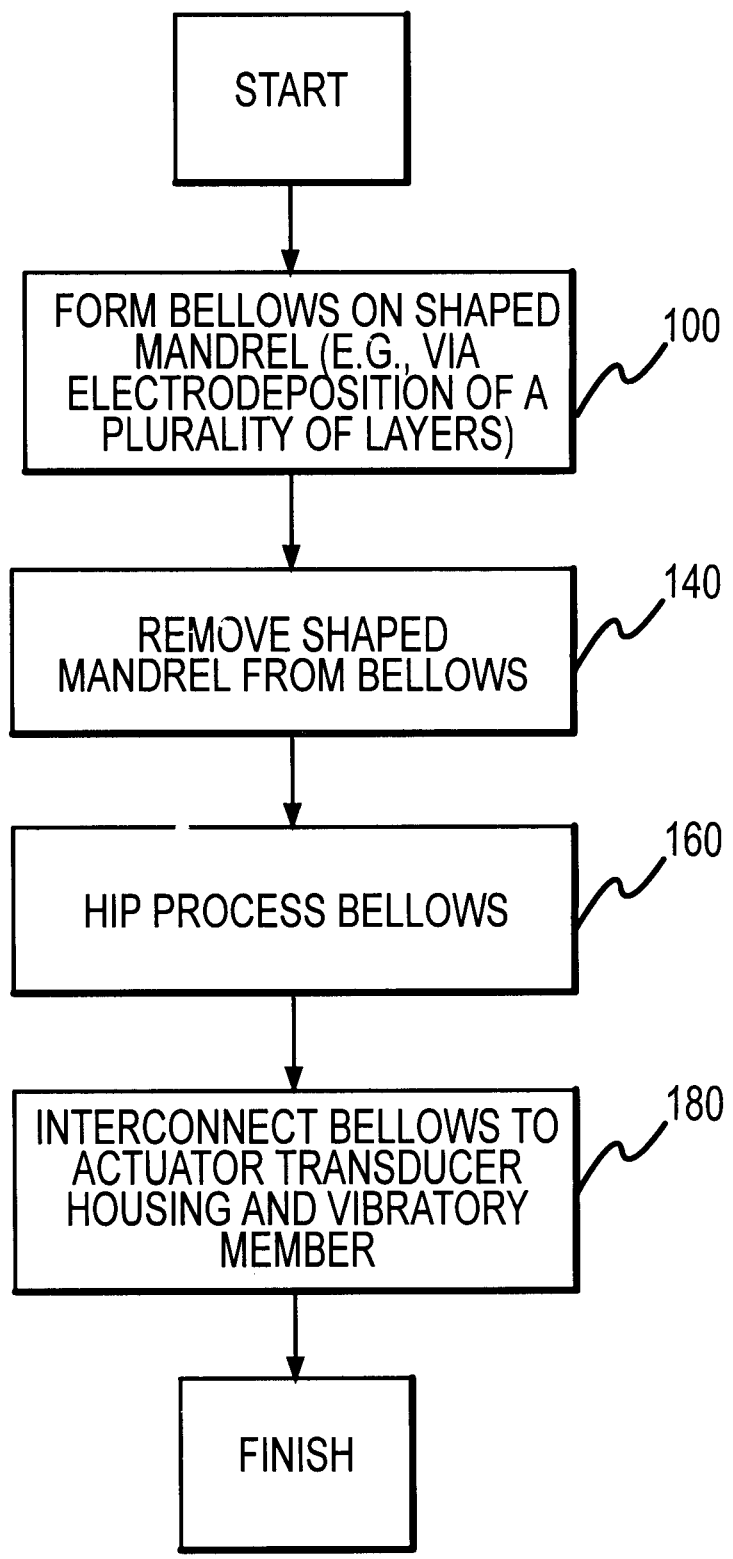
FIG. 3 is a process flow diagram directed to the manufacture/implementation of the bellows of FIG. 2 into the embodiment of FIG. 1.

FIG. 3 generally illustrates one embodiment of a process for fabrication/implementation of bellows 30. Such embodiment provides for the initial formation of bellows 30 via the sequential electrodeposition of a plurality of layers 31, 33 and 35 on a shaped mandrel 200 (step 100). Utilization of electrodeposition processing yields enhanced sealing of the various layers of bellows 30. Following bellows 30 formation, the shaped mandrel 200 may be selectively removed therefrom (step 140), thereby facilitating complex configurations for bellows 30. Then, in order to enhance the fatigue properties of bellows 30, bellows 30 may be subjected to hot isostatic processing (step 160). Finally, bellows 30 may be interconnected to transducer 10 and vibratory member 20 in a manner that yields reliable sealing therebetween (step 180).

Figure 2:
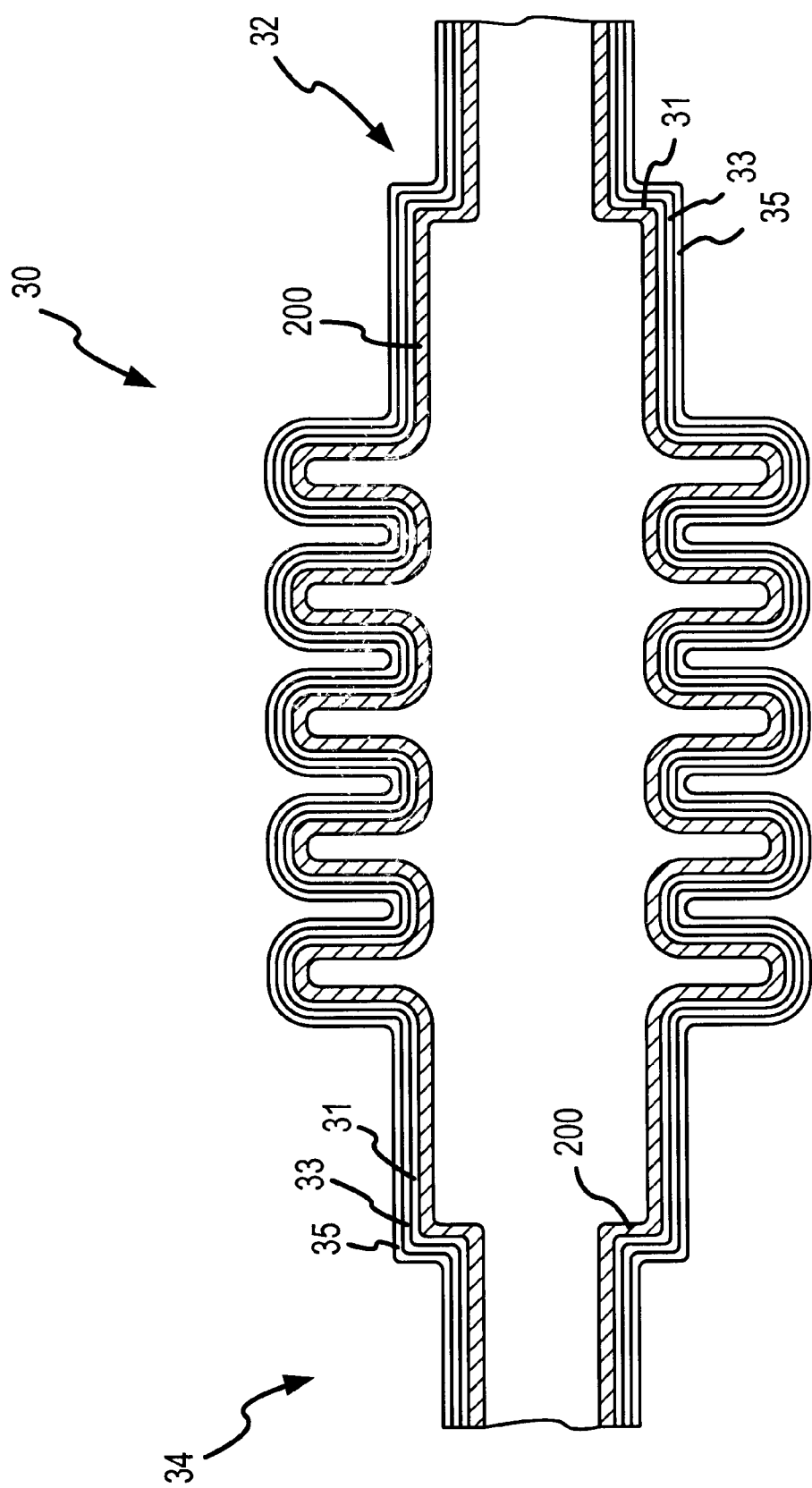
FIG. 2 is a cross-sectional side view of a bellows employable in the embodiment of FIG. 1.
Figure 4:
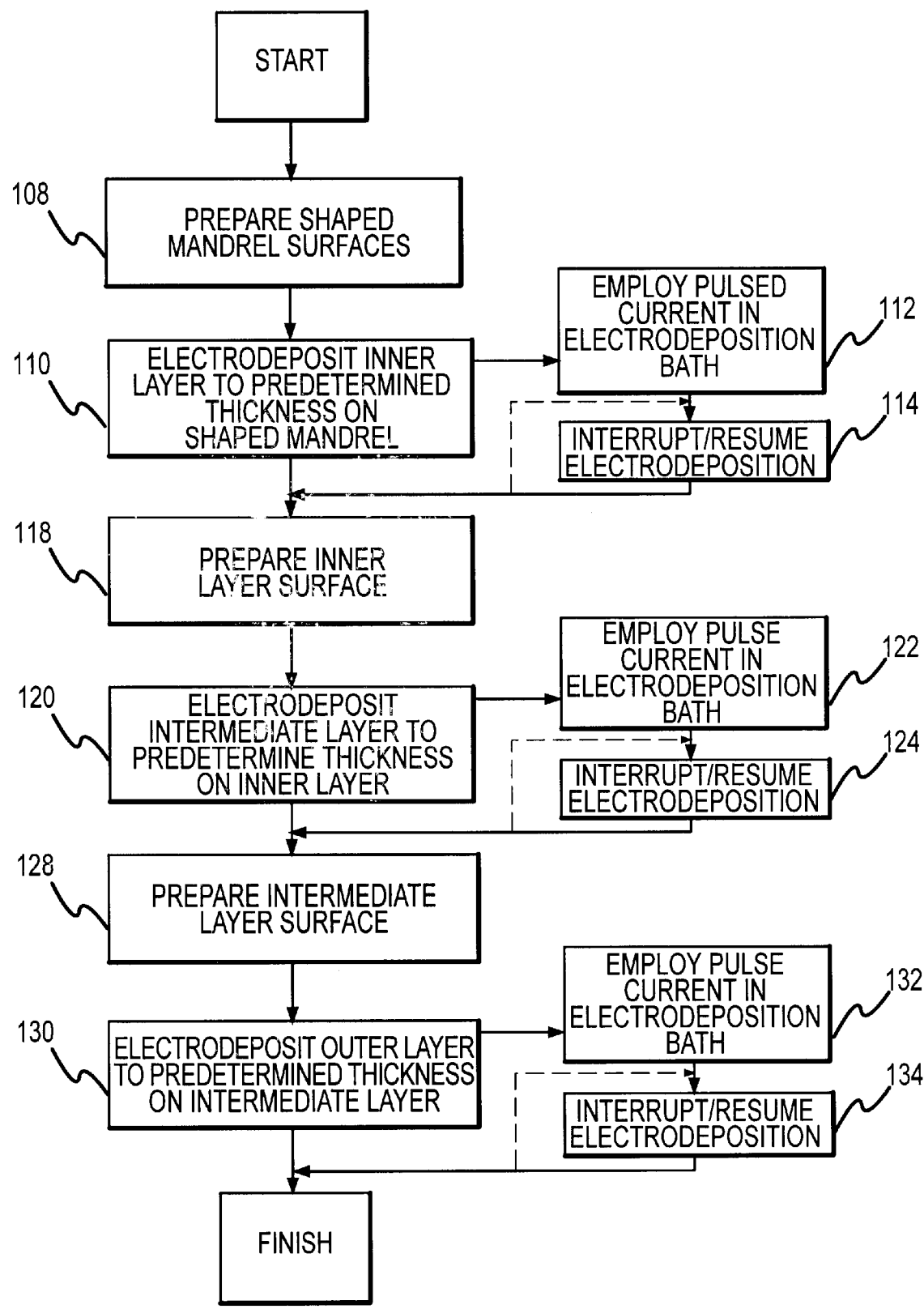
FIG. 4 is a process flow diagram for one embodiment directed to the sequential electrodeposition of layers to form the bellows of FIG. 2.

Referring now to FIG. 4, the electrodeposition formation of bellows 30 (i.e., step 100) is illustrated as comprising separate and sequential steps for the electrodeposition of inner layer 31 (step 110), intermediate layer 33 (step 120) and outer layer 35 (step 130), and correspondingly surface preparation steps (steps 108, 118 and 128). More particularly, inner layer 31 may be formed via the electrodeposition of an appropriate material (e.g., as noted above) on a supporting shaped mandrel 200. As shown in FIG. 2, the shaped mandrel 200 may be configured to define the desired undulating configuration of bellows 30. Preparation of the outer surfaces of mandrel 200 (step 108) may entail surface cleaning (e.g. with methylene chloride), stripping trapped metals, surface preservation (e.g. using a zincate bath), and surface conditioning (e.g. striking the surface in an electroless nickel bath to enhance surface uniformity and/or striking the surface in an aluminum plating bath to yield an adherent layer).

The electrodeposition of inner layer 31 may be achieved via submersion of the shaped mandrel 200 in a plating bath (e.g. gold), wherein an electrical current is passed through the shaped mandrel to additively build up the inner layer 31 to a predetermined thickness. In this regard, it has been recognized that a pulsed current may be provided to the shaped mandrel (step 112), wherein the plating bath nucleates in conjunction with each pulse to reduce the likelihood of pore formation in inner layer 31. Further, the electrodeposition of inner layer 31 may be completed in a plurality of substeps, wherein a corresponding plurality of inner layer 31 sublayers are successively formed. In conjunction with each such substep the electrodeposition process may be interrupted/resumed to affect grain boundary discontinuities (step 114). For example, the application of the electrical current may be stopped/restarted. Additionally or alternatively, the mandrel 200 may be removed from and then resubmerged into the plating bath. The formation of one or more sublayers of inner layer 31 during electrodeposition build-up further enhances the protective sealing function of inner layer 31. In particular, the utilization of such an approach reduces bodily fluid access through undesired pores since, with multiple sublayers, it is unlikely that undesired pores in the different sublayers will be aligned to provide fluid access therethrough.

As shown by FIG. 4, intermediate layer 33 may be formed via the electrodeposition of an appropriate material (e.g., as noted above) on the inner layer 31. Preparation of the surface of inner layer 31 (step 118) may entail surface cleaning, (e.g. using ultrasound techniques and surface activation (e.g. with a hot sulfuric acid bath). The electrodeposition of intermediate layer 33 may be achieved via submersion of the shaped mandrel 200 with inner layer 31 into a plating bath (e.g. nickel), wherein an electrical current is passed through the shaped mandrel 200 to additively build-up the intermediate layer 33 to a predetermined thickness. As with the formation of inner layer 31, it has been recognized that a pulsed current may be utilized (step 122), wherein the plating bath nucleates in conjunction with each pulse to reduce the likelihood of pore formation in intermediate layer 33. Further, electrodeposition of intermediate layer 33 may also be completed in a plurality of substeps, wherein a corresponding plurality of intermediate layer 33 sublayers are successively formed. In conjunction with such substeps, the electrodeposition process may be interrupted/resumed (step 124). Again, the formation of two or more sublayers of intermediate layer 33 during electrodeposition build-up may further enhance sealing.

Referring further to FIG. 4, the formation of the outer layer 35 may also be completed via electrodeposition of an appropriate material (e.g., as noted above) on the intermediate layer 33. Preparation of the surface of intermediate layer 33 (step 128) may entail surface cleaning, surface smoothing (e.g. using an actane bath), surface activation (e.g. with a hot sulfuric acid bath) and surface conditioning (e.g. striking the surface with an aluminum plating bath to yield an adherent surface). The completion of layer 35 may be achieved via submersion of the shaped mandrel 200 with inner layer 31 and intermediate layer 33 in an appropriate plating bath (e.g. gold) wherein an electrical current is passed through the shaped mandrel 200 to additively buildup outer layer 35 to a predetermined thickness. Again, it has been recognized that a pulsed current may be provided to the shaped mandrel (step 132) wherein the plating bath nucleates in conjunction with each pulse to reduce the likelihood of pore formation in outer layer 35. Further, electrodeposition of outer layer 35 may be completed in a plurality of substeps, wherein a corresponding plurality of sublayers portions are successively formed to define outer layer 35. In conjunction with each such substep the process may be interrupted/resumed (step 134). Again, the formation of multiple sublayers of outer layer 35 during electrodeposition build-up enhances sealing.

Figure 5:
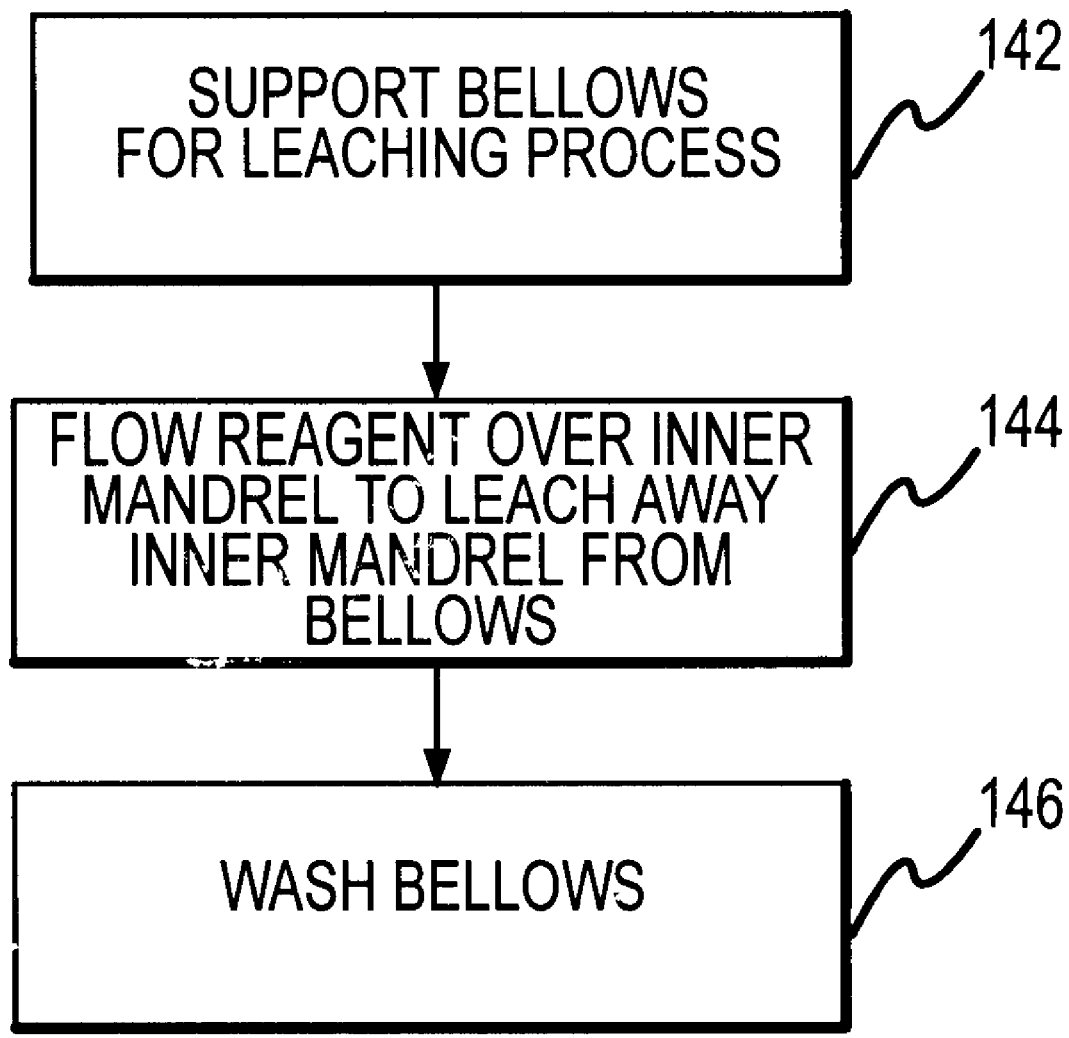
FIG. 5 is a process flow diagram illustrating steps of an embodiment for removing a shaped mandrel in connection with the formation of the bellows of FIG. 2.

As previously noted, the above-noted shaped mandrel 200 utilized in the formation of bellows 30 may be selectively removed. In this regard, a collapsible mandrel may be employed. Alternatively, and more preferably, a removal fluid and may be utilized. In this regard, and referring now to FIG. 5, the mandrel 200 and bellows 30 may be supported in a reservoir (step 142), and an appropriate reagent may be flowed through the shaped mandrel 200 to leach the shaped mandrel away from the formed bellows 30 (step 144). As will be appreciated, the utilization of such a leaching process entails the utilization of materials for the shaped mandrel and inner layer 31 of bellows 30 which are leachable and non-leachable, respectively, in the presence of the reagent utilized. By way of example, an inner layer 31 comprising gold and a hollow shaped mandrel 200 comprising aluminum have been satisfactorily utilized in conjunction with a sodium hydroxide reagent. Following removal of the shaped mandrel 200 from the formed bellows 30, the bellows 30 may be washed (step 146) prior to further processing. Other embodiments may provide for dissolving the mandrel 200 in a selected solvent or melting the mandrel in a heated bath.

Figure 6:
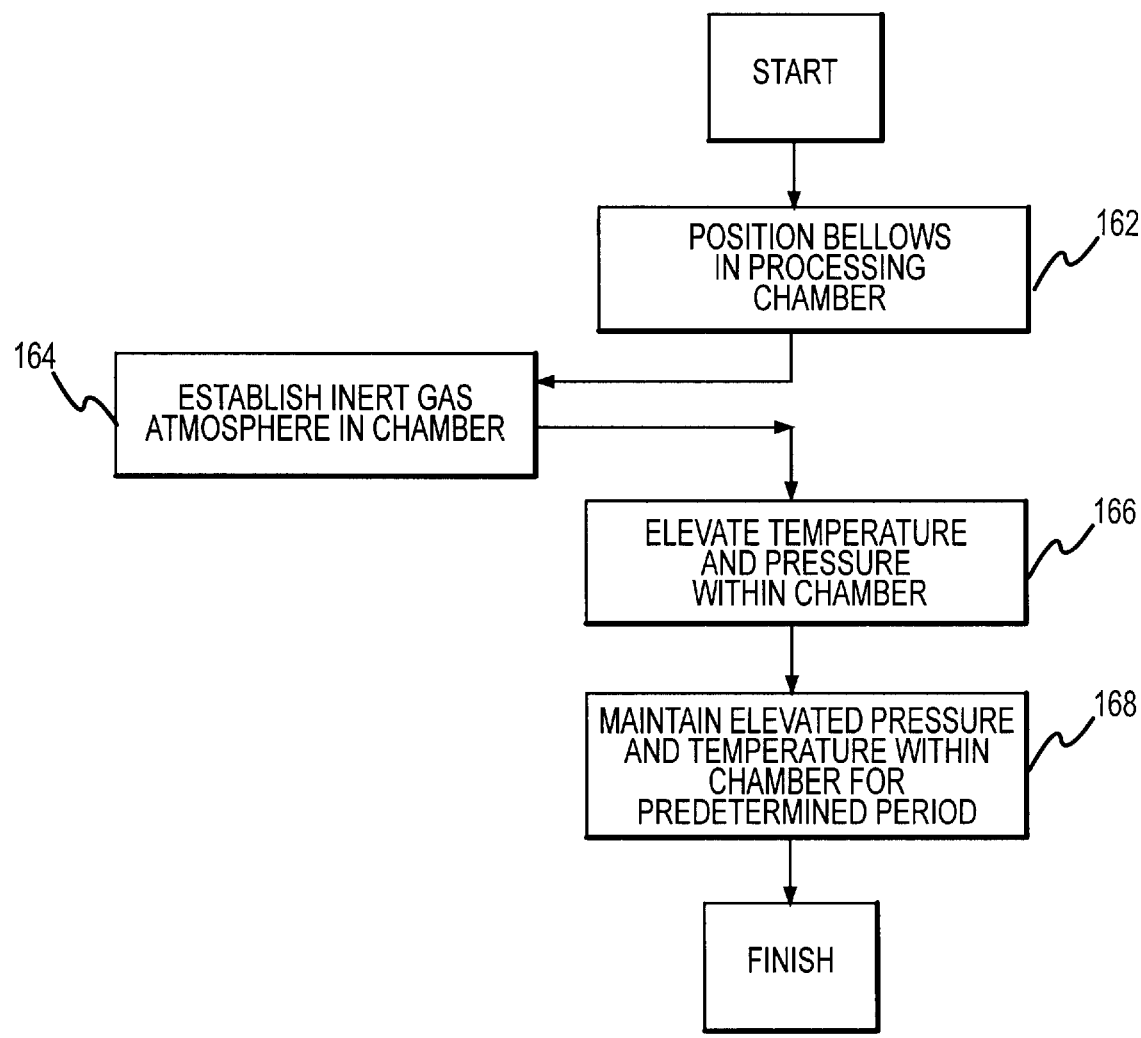
FIG. 6 illustrates one embodiment of a hot isostatic technique employable in conjunction with the formation of the bellows of FIG. 2.

As noted in the process embodiment of FIG. 3, bellows 30 may be advantageously subjected to hot isostatic pressing (HIP). To further describe such processing, reference is now made to FIG. 6. As illustrated, bellows 30 may be positioned in an appropriate processing chamber in which the atmosphere/temperature/pressure are selectively controllable (step 162). For example, an inert gas atmosphere (e.g. argon) may be established (step 164), and the temperature and pressure within the chamber may be increased (step 166) so that the yield strength of one or more layers of bellows 30 (e.g. layer 33) is less than the set pressure at the set temperature. The elevated pressure and temperature within the chamber may then be maintained for an appropriate time period (step 168) to close and diffusion bond internal pores within the intended affected layer.

By way of example, in an arrangement having a bellows 30 with an inner layer 31, intermediate layer 33, and outer layer 35, comprising gold, nickel and gold, respectively, with each layer having a thickness of about 10 microns, HIP processing has been satisfactorily completed utilizing an argon atmosphere with elevated temperatures and pressures of at least about 400° C. and 15,000 psi for a predetermined period of at least about 30 minutes. The utilization of HIP processing functions to enhance the microstructure of the intermediate layer 33. Such modification in turn yields enhanced fatigue characteristics.

Figure 8A:
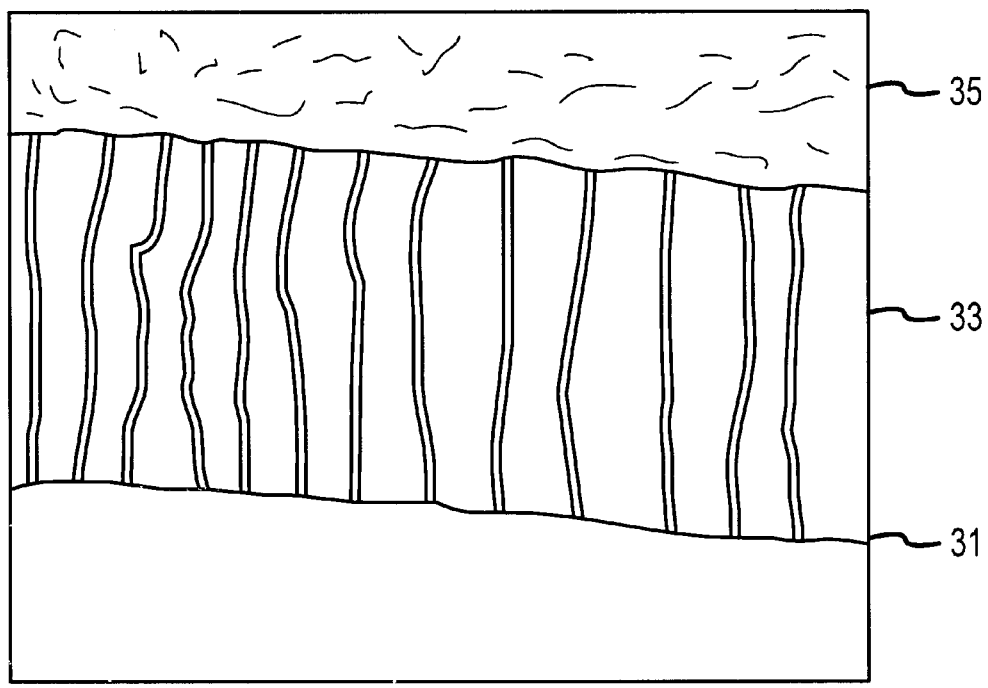
FIGS. 8A and 8B illustrate exemplary microstructures associated with the bellows of FIG. 2 prior to and after the utilization of the process refinement illustrated in FIG. 6.
Figure 8B:
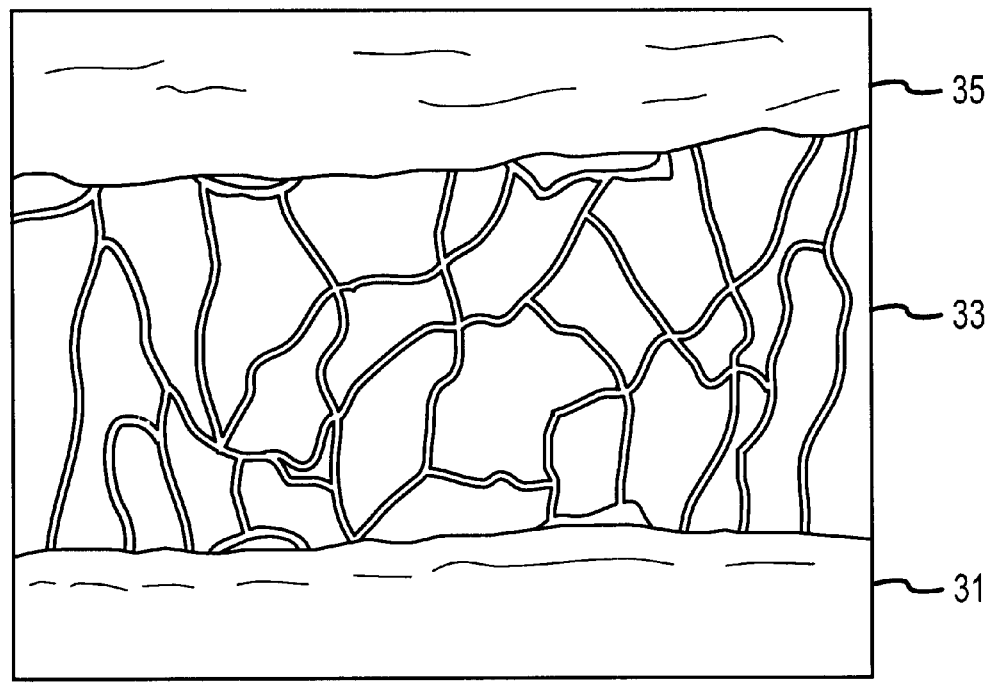

In this regard, FIGS. 8A and 8B illustrate the microstructure of a bellows 30 comprising gold, nickel and gold layers prior to and after HIP processing. As can be seen in FIG. 8A, the intermediate nickel layer is of a columnar microstructure. After HIP processing, FIG. 2 illustrates how the nickel layer has been modified to a more relatively isotropic granular microstructure.

Figure 7:
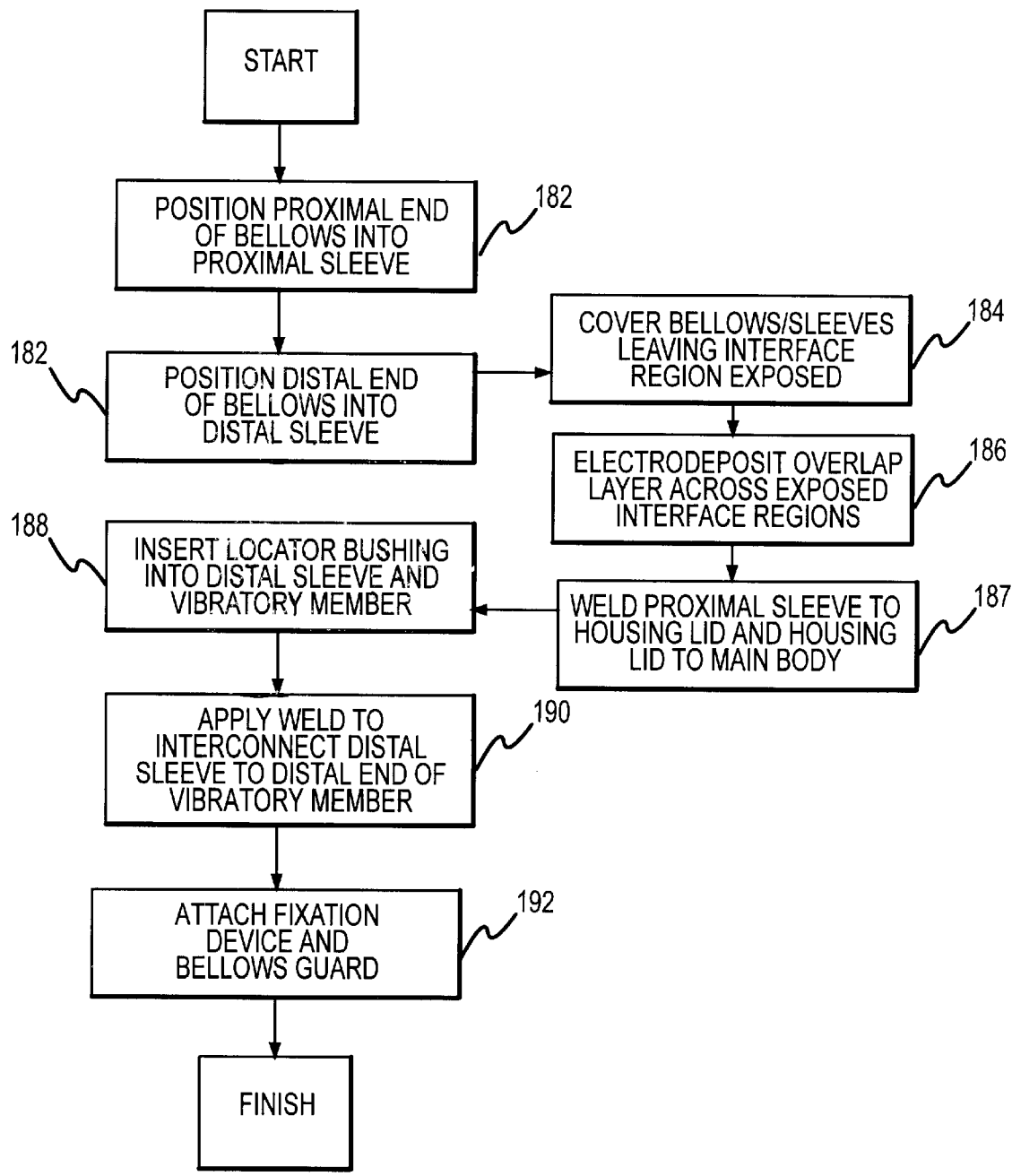
FIG. 7 is a process flow diagram for one embodiment for interconnecting the bellows of FIG. 2 in the embodiment of FIG. 1.

Referring now to FIG. 7, a further process diagram is illustrated showing key steps in one process embodiment for interconnection of bellows 30 in an actuator embodiment as per FIG. 1. In particular, the above-noted tang 31 at the proximal end 32 of bellows 30 may be positioned (e.g. slidably inserted) into the proximal sleeve 70 (step 182). Then, the above-noted tang 33 at the distal end 34 of bellows 30 may be positioned (e.g. slidably inserted) within the proximal end of distal sleeve 80 (step 184) to define a 3-part assembly. Prior to such assembly, the outer layer 35, intermediate layer 33 and a portion of the inner layer 31 may be selectively removed from the opposing ends of bellows 30 (e.g. via bead blasting with the undulating central portion of bellows 30 protectively shielded), wherein the noted tangs 31, 33 comprise only the remaining portion of inner layer 31. Then, a proximal end of proximal sleeve 70, a central portion of bellows 30 and a distal end portion of distal sleeve 80 may be covered (e.g. with inflatable silicon boots), leaving only the abutment regions therebetween exposed (step 184). Such exposed regions of the sleeves 70, 80 may be pretreated (e.g. gold-plated). Thereafter, the 3-part assembly may be submerged in a plating bath to electrodeposit a biocompatible metal (e.g. gold) onto the uncovered abutment regions (step 186), thereby simultaneously defining layers 70, 72 noted above. In one arrangement two successive gold plating baths have been utilized to define layers 70, 72.

Preferably, steps 182, 184 and 186 are completed prior to removal of the shaped mandrel 200 from billons 30 described above. More particularly, mandrel 200 may be utilized to support the noted 3-part assembly during the electrodeposition step 186. For such purposes mandrel 200 may be configured to slidably receive the sleeves 60, 80 at opposing ends with the formed bellows 30 interposed therebetween.

Following formation of layers 70, 72, the proximal end of 62 proximal sleeve 60 may be laser welded to housing lid 54, and housing lid 54, may be laser welded to housing body 52 (step 187). As previously indicated, a bushing 90 may then be inserted into the distal end 84 of distal sleeve 80, and a wire section 92 may be positioned within the end of vibratory member 20 (step 188). Thereafter, the distal sleeve 80, vibratory member 20, and wire member 92 may be putter welded together to hermetically seal the distal interconnections therebetween (step 190). Finally, a tip assembly 94 may be tack welded about the distal end of distal sleeve 80 and a bellows guard 96 may be positioned about the bellows 30 (step 192).

The embodiment descriptions provided above are for exemplary purposes only and are not intended to limit the scope of the present invention. Various modifications and extensions of the described embodiments will be apparent to those skilled in the art and are intended to be within the scope of the invention as defined by the claims which follow.

What is claimed is:

1. An implantable hearing aid apparatus comprising:
   first and second implantable hearing aid component housing members; and
   at least one electrodeposited layer overlapping adjacent portions of said first and second housing members.

2. An implantable hearing aid apparatus as recited in claim 1, wherein said at least one electrodeposited layer includes:
   an outer electrodeposited layer comprising a biocompatible material.

3. An implantable hearing aid apparatus as recited in claim 2, wherein said biocompatible material is a biocompatible metal selected from a group consisting of gold, titanium and platinum.

4. An implantable hearing aid apparatus as recited in claim 2, wherein said at least one electrodeposited layer further includes:
   an underlying electrodeposited layer hermetically sealed on one side by said outer electrodeposited layer, wherein said underlying layer comprises a material different than that of said electrodeposited outer layer.

5. An implantable hearing aid apparatus as recited in claim 4, wherein said underlying layer has at least one of a modulus of elasticity, tensile strength and yield strength that is at least two times greater than that of the outer electrodeposited layer.

6. An implantable hearing aid apparatus as recited in claim 4, wherein said underlying electrodeposited layer comprises a material selected from a group consisting of: nickel, iron, chromium, iridium, copper and aluminum.

7. An implantable hearing aid apparatus as recited in claim 6, wherein said at least one electrodeposited layer further includes:
   an inner electrodeposited layer hermetically sealing another side of said underlying layer.

8. An implantable hearing aid apparatus as recited in claim 7, wherein said inner electrodeposited layer comprises a biocompatible material.

9. An implantable hearing aid apparatus as recited in claim 8, wherein said biocompatible material is a biocompatible metal selected from a group consisting of gold, titanium and platinum.

10. An implantable hearing aid apparatus as recited in claim 1, wherein adjacent portions of said first and second implantable housing members are configured to define a substantially flush interface region therebetween.

11. A method as recited in claim 10, wherein said at least one electrodeposited layer is at least one of substantially continuously arcuate and substantially planar.

12. An implantable hearing aid apparatus comprising:
    a first housing member comprising a plurality of electrodeposited layers, wherein at least two adjacent ones of said plurality of electrodeposited layers comprise differing materials.

13. An implantable hearing aid apparatus as recited in claim 12, wherein said plurality of electrodeposited layers includes:
    an outer electrodeposited layer comprising a biocompatible metal selected from a group consisting of gold, titanium and platinum.

14. An implantable hearing aid apparatus as recited in claim 13, wherein said plurality of electrodeposited layers further includes:

an underlying electrodeposited layer hermetically sealed on one side by said outer electrodeposited layer, wherein said underlying layer comprises a metal selected from a group consisting of nickel, iron, chromium, iridium, copper and aluminum.

15. An implantable hearing aid apparatus as recited in claim 14, wherein said plurality of electrodeposited layers further includes:

an inner electrodeposited layer hermetically sealing another side of said underlying layer.

16. An implantable hearing aid apparatus as recited in claim 15, wherein said inner electrodeposited layer comprises a biocompatible material.

17. An implantable hearing aid apparatus as recited in claim 16, wherein said biocompatible material is selected from a group consisting of gold, titanium and platinum.

18. An implantable hearing aid apparatus as recited in claim 12, wherein said plurality of electrodeposited layers includes:

an outer layer comprising a first material; and, an underlying layer comprising a second material having at least one of a modulus of elasticity, yield strength and tensile strength that is at least two times that of the outer layer.

19. An implantable hearing aid apparatus as recited in claim 18, wherein said plurality of electrodeposited layers further includes:

an inner layer, wherein said inner layer and outer layer hermetically seal the underlying layer therebetween.

20. An implantable hearing aid apparatus as recited in claim 12, further comprising:

a second implantable hearing aid component housing member; and, a first electrodeposited interconnection layer overlapping adjacent portions of said first and second housing members.

21. An implantable hearing aid apparatus as recited in claim 20, further comprising:

a third implantable hearing and component housing member; and, a second electrodeposited interconnection layer overlapping adjacent portions of the third and second housing members.

22. An implantable hearing aid apparatus as recited in claim 21, wherein a distal end of said first housing member abuts said second housing member to define a substantially planar abutment region therebetween, and wherein a proximal end of said first housing member abuts said third housing member to define a substantially planar abutment region therebetween.

23. An implantable hearing aid apparatus as recited in claim 22, wherein said first electrodeposited interconnection layer overlaps said substantially planar abutment region between first and second housing members, and wherein said second electrodeposited interconnection layer overlaps said substantially planar abutment region between said first and second housing members.

24. An implantable hearing aid apparatus as recited in claim 21, wherein said first electrodeposited interconnection layer and said second electrodeposited interconnection layer each comprise a biocompatible material.

25. An implantable hearing aid apparatus as recited in claim 24, wherein said biocompatible material is a biocompatible metal selected from a group consisting of: gold, titanium and platinum.

26. An implantable hearing aid apparatus comprising:

a transducer disposed within a housing;

a vibratory member having a proximal end interconnected to said transducer and having a distal end extending through and away from said housing; and, a hollow bellows member interconnected at a proximal end to said housing and interconnected at a distal end to said vibratory member, said hollow bellows member having an undulating configuration between said proximal and distal ends that is defined by a plurality of conformal layers, wherein said plurality of conformal layers includes an inner layer, an outer layer and intermediate layer disposed between said inner and outer layers, and wherein adjacent ones of said inner layer, intermediate layer and outer layer comprise different materials.

27. An implantable hearing aid actuator as recited in claim 26, wherein said inner layer comprises a material selected from a group consisting of: gold, titanium and platinum; and wherein said outer layer comprises a material selected from a group consisting of: gold, titanium and platinum.

28. An implantable hearing aid actuator as recited in claim 26, wherein said intermediate layer comprises a material selected from a group consisting of nickel, steel and iron.

29. An implantable hearing aid actuator as recited in claim 26, wherein said intermediate layer has a modulus of elasticity that is greater than that of the outer layer and the inner layer.

30. An implantable hearing aid actuator as recited in claim 26, wherein said proximal end and said distal end of said hollow bellows member each include a stepped-in portion, and further comprising:

proximal and distal sleeve members partially disposed about and abutting with said stepped-in portions of said proximal and distal ends, respectively, of the hollow bellows member, wherein the proximal sleeve member is rigidly interconnected to said vibratory member and the distal sleeve member is rigidly interconnected to said housing.

* * * * *